United States Patent [19]

Schlossman et al.

[11] Patent Number: 4,649,106

[45] Date of Patent: Mar. 10, 1987

[54] DISTINGUISHING SUBSETS OF HUMAN CELLS

[75] Inventors: Stuart F. Schlossman, Newton Center; Chikao Morimoto, Needham, both of Mass.

[73] Assignee: Dana-Farber Cancer Institute, Inc., Boston, Mass.

[21] Appl. No.: 616,284

[22] Filed: Jun. 1, 1984

[51] Int. Cl.⁴ .................... G01N 33/53; G01N 33/554
[52] U.S. Cl. ........................................... 435/7; 435/29; 435/34; 435/68; 435/171.2; 435/240; 436/519; 436/548; 530/387; 935/95; 935/101; 935/110
[58] Field of Search ...................... 260/112 R; 424/85; 435/29, 34, 171.2, 240, 7; 436/519, 548; 935/105, 110, 101; 530/387

[56] References Cited

U.S. PATENT DOCUMENTS

| | | | |
|---|---|---|---|
| 4,363,799 | 12/1982 | Kung | 435/240 X |
| 4,364,932 | 12/1982 | Kung | 435/240 X |
| 4,364,937 | 12/1982 | Kung | 436/548 X |
| 4,381,292 | 4/1983 | Bieber | 436/548 X |
| 4,474,893 | 10/1984 | Redding | 424/85 X |
| 4,511,662 | 4/1985 | Baran | 436/519 X |

OTHER PUBLICATIONS

"Essential Immunology", Fourth Edition, by Ivan Roitt, pp. 51–53, Blackwell, Scientific Publications, London, 1980.
Reinherz, E. L. et al., Immunology Today, 4(1), 5–8 (1983).
Reinherz et al. (1980), Cell, 19, 821–827.
Reinherz et al. (1981), Jour. of Immun., 126, 67–70.
Dvorak et al. (1978), Jour. of Immun., 120(4), 1240–1248.
Morimoto et al. (1981), J. Clin. Invest., 67, 753–761.
Thomas et al. (1980), Journ. of Immun., 125, 2402–8.
Gatenby et al. (1982), J. Exp. Med., 156, 55–67.
Yachi et al. (1982), Journ. of Immun., 179, 103–107.
Reinherz et al. (1982), Jour. of Immun., 128(1), 463–468.
Morimoto et al. (1982), Jour. of Immun., 128(4), 1645–1650.
Parham et al. (1980), Immunogenetics, 11, 131–143.
Neubauer et al. (1982), Jour. of Immunogenetics, 9, 209–221.
Haynes et al. (1982), Science, 215, 298–300.
Sanderson et al. (1981), Immunology, 44, 169–175.
Rogers et al. (1982), Fed. Eur. Biochem. Soc., 146(1), 93–96.
Ellingsworth et al. (1981), Vet. Immun. and Immunopath., 2, 541–553.
Marchalonis et al. (1981), Jour. of Immunogenetics, 8, 165–175.
Marchalonis et al. (1980), Proc. Natl. Acad. Sci. USA, 77(6), 3625–3629.
Martin et al (1981), Fed. Proc., 40, 995, Abstract No. 4334.

*Primary Examiner*—Sidney Marantz

[57] ABSTRACT

A method of distinguishing subsets within a plurality of human cells including producing a monoclonal antibody to a non-human primate cell, contacting the monoclonal antibody with the human cells, and distinguishing the subsets on the basis of different degrees of reactivity with the monoclonal antibody.

7 Claims, 3 Drawing Figures

DISTINGUISHING SUBSETS OF HUMAN CELLS

BACKGROUND OF THE INVENTION

This invention relates to monoclonal antibodies.

Recent developments in hybridoma technology have demonstrated that human T cells can be divided into more than one functionally distinct subpopulation. For example, Reinherz et al., *Cell,* 19:821 (1980) and Reinherz et al., Immunology Today, 4:69 (1981) describe studies which indicate that certain T cell subsets have inducer functions, whereas other subsets have suppressor functions. Other studies have demonstrated that communicative interactions occur between and within the major T cell subsets in the generation of specific effector functions; Evans et al., J. Immunol., 120:1243 (1978); Morimoto et al., J. Immunol., 128:1645 (1982); Thomas et al., J. Immunol. 125:2402 (1980); Gatenby et al., J. Exp. Med., 156:55 (1982); and Yachi et al., J. Immunol., 129:103 (1982). Because regulatory mechanisms are essential to the maintenance of immune homeostasis, an understanding of the interactions between the subsets is of considerable importance.

It has been shown that within the major T cell sets T4 and T8 there exists both functional and phenotypic heterogeneity; Thomas et al., *J. Immunol.,* 125: 2402 (1980); Morimoto et al., *J. Immunol.,* 128: 1645 (1982); Gatenby et al., *J. Exp. Med.,* 156: 55 (1982); and Reinherz et al., *J. Immunol.,* 126: 67 (1981). Interaction between subpopulations of T4 and T8 cells, for example, is required to induce suppression of IgG production in antigen, pokeweed mitogen, or autologous leukocyte reaction-driven systems. Similarly, differentiation of T8 cytotoxic effectors from precytotoxic T8 lymphocytes in mixed leukocyte reactions has been shown to require the presence of T4 cells.

A number of monoclonal and autoantibodies have been developed which have provided an initial phenotypic definition of the heterogeneity within the major populations of these cells. Morimoto et al., *J. Clin. Invest.,* 67: 753 (1981) describes using naturally occurring anti-T cell antibodies found in some patients with active juvenile rheumatoid arthritis (JRA) to subdivide T4 cells into helper population (T4JRA−) and an inducer of suppressor subpopulation (T4JRA+) for pokeweed mitogen and antigen driven immunoglobulin production. Similarly, Reinherz et al., *J. Immunol.,* 128: 463 (1982) describes using antibody to Ia to divide T4 cells into T4Ia+ and T4Ia−subsets; both subsets were required to induce optimal Ig secretion by B cells.

SUMMARY OF THE INVENTION

In general, the invention features a method of distinguishing subsets within a plurality of human cells, preferably T cells such as T4 cells, which method includes producing a monoclonal antibody to a non-human primate cell such as a marmoset or chimpanzee T cell, contacting the monoclonal antibody with the human cells, and distinguishing the subsets on the basis of different degrees of reactivity with the monoclonal antibody.

The method of the invention permits the division of an otherwise apparently homogeneous population (or "set") of human cells into unique subpopulations (or "subsets"). In the case of T cells, this dissection into subsets can be correlated with the existence of polymorphic determinants which can be used as markers of disease susceptibility, in particular autoimmune diseases such as Juvenile Rheumatoid Arthritis (JRA), Sjogren's disease, and Systemic Lupus for Erythermatosis (SLE), in which T cells are implicated. Also, the fact that a seemingly homogeneous population of T4 cells can be dissected into subsets, which may be functionally distinct, helps explain the great heterogeneity, in terms of clinical patterns, which exists in diseases such as JRA and SLE, but which do not correlate with simple measurements of T4 cells.

Immunization with a non-human primate cell thus can produce a monoclonal antibody which reacts to a greater degree with a first subset of a set of human cells than with a second subset, even though the two subsets exhibit substantially the same degree of reactivity with a different monoclonal antibody which defines the set; e.g., an antibody highly reactive with T4 cells but exhibiting little reactivity with T8 cells. Preferably the human cells are lymphocytes, e.g., B cells or T cells such as T4 or T8 cells.

It has been discovered that an additional benefit is realized by immunization with non-human primate cells: for reasons which are as yet unclear, antigenic determinants common to a human and a non-human primate cell sometimes can exhibit greater immunogenicity in rodents, e.g., mice, when presented on the non-human cell, compared to the human cell. This may be because of a comparatively greater immunodominance of some determinants on non-human primate cells, perhaps owing to the expression of the determinant on the non-human cell in a more highly antigenic configuration. This discovery makes possible increased production of monoclonal antibodies against important but weakly antigenic determinants on human cells, by immunizing with a non-human primate cell also bearing the determinant.

Referring now to FIG. 1, the method of using non-human primate cells to produce a monoclonal antibody capable of dividing a set of human cells into subsets can be carried out an additional step, to produce a monoclonal antibody which is specific for one of the subsets, as follows. Once a non-human primate-derived monoclonal antibody has been used to identify two distinct subsets of, say, human T4 cells (one subset being more reactive and the other less reactive with the antibody), one of the identified subsets (say the more reactive subset) can be used to immunize mice to produce a plurality of hybridomas; the monoclonal antibodies produced by these hybridomas can then be screened against the immunizing subset and the other subset. An antibody more reactive with the immunizing subset than with the other subset defines the polymorphic surface structure or structures which differentiate the two subsets.

Such an antibody could be useful in the diagnosis and/or treatment of a disease, e.g., JRA, caused or exacerbated by the immunizing subset. Diagnosis could be accomplished using flow cytometry to measure reactivity of cells, with the antibody conjugated with a fluorescent dye. To treat the disease, the antibody could be chemically coupled to a cytotoxic agent and administered to a patient suffering from the disease. The antibody would specifically bind to and destroy the disease-causing cells, but not the normal cells.

Other features and advantages of the invention will be apparent from the following description of the preferred embodiments thereof, and from the claims.

DESCRIPTION OF THE PREFERRED EMBODIMENTS

The drawings will first be described.

Drawings

IMMUNIZATION WITH NON-HUMAN PRIMATE CELLS

Figure 1:
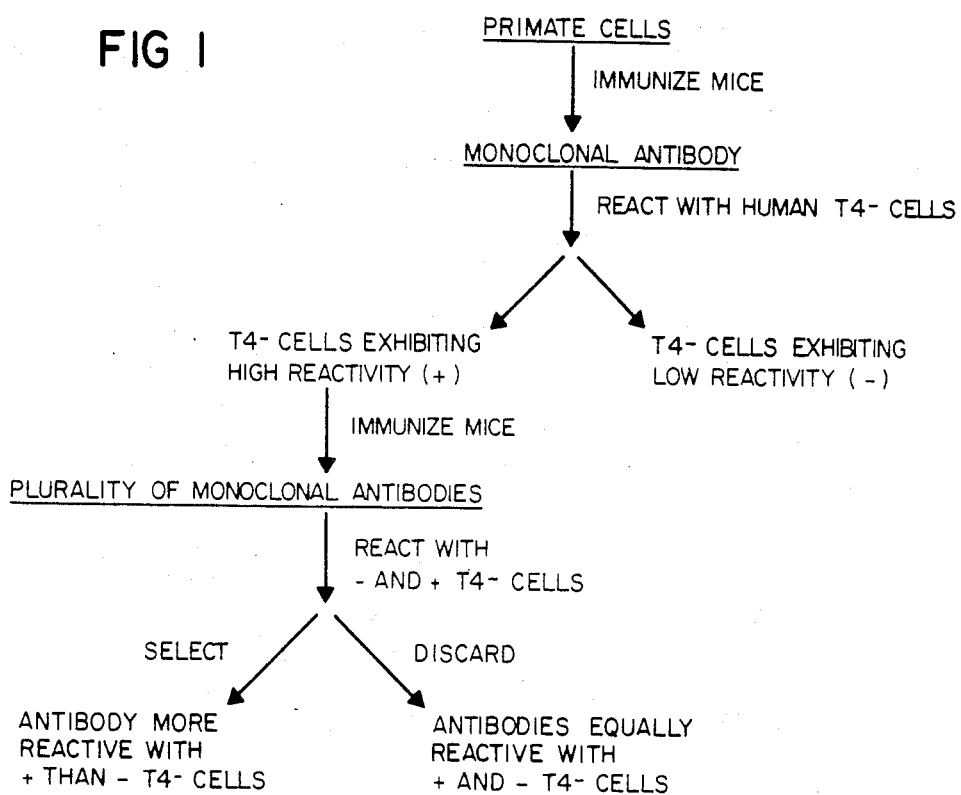
FIG. 1 is a flow chart of an antibody production method, discussed above.
Figure 3:
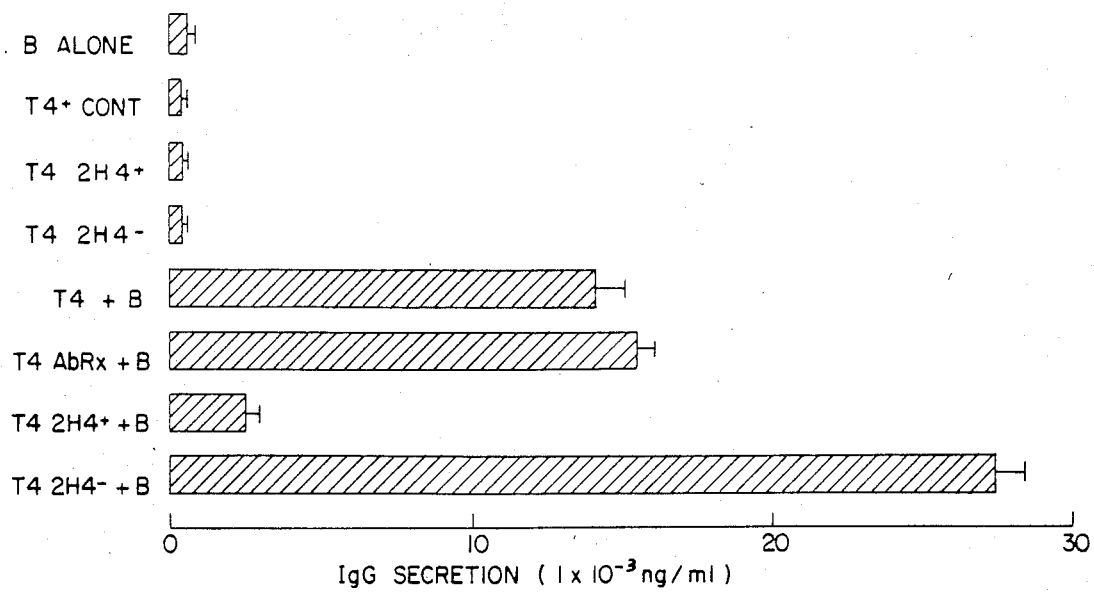
FIG. 3 is a histogram showing induction of help by various cells and cell combinations.

The first step in the method is to select the non-human primate whose cells are to be used for immunization. The choice of primate depends in part on how phylogenetically distant the primate is from humans. This phylogenetic distance is generally reflected in the reactivity of a primate's cells with monoclonal antibodies of human origin.

Table 1, below, shows the reactivities of T-cells of various species with monoclonal antibodies produced by immunizing Balb/C or CAF1 mice with a variety of human T-cell subsets. Cells of chimpanzees, phylogenetically close to humans, react with all of the human cell-derived antibodies, while cells of the distant lemur react with none. Common marmoset T-cells are reactive with T4A and T8A, but with none of the other antibodies.

cells, T4JRA-TQ1+, T4JRA-TQ1−, T8 cells, T4 cytotoxic lines, T8 cytotoxic lines, T4 antigen specific inducer T cell lines, T4 antigen specific inducer of suppressor T cell lines, T8 suppressor lines, and freshly isolated activated T cells. Antibodies which are reactive with a fraction of the inducer or suppressor population but unreactive with human B lymphocytes, B cell lines, myeloid cells, and myeloid lines are isolated.

Such antibodies can then be used to divide a T4 or T8 population into subsets, based on the degree to which cells from each subset react with the antibodies. Such different reactivities will indicate either the existence of polymorphic epitopes in the structure of a single surface antigen which defines, say, T4 or T8; or the existence of a family of such surface antigens which define the T4 and T8 population, which family of antigens exhibits heterogeneity. In either case, the polymorphism or heterogeneity can be detected using primate-derived monoclonal antibodies. Given the variety of abnormalities in immunoregulatory subsets that exist in a number of autoimmune diseases, the definition of either polymorphic determinants or unique subsets can prove to be very important, given the existing evidence that variations in structures of the MHC complex are of importance in predicting disease susceptibility.

Antibodies that react with subfractions of T4 and T8 populations of cells are characterized by indirect immunofluorescence, as follows. Approximately $10^6$ cells are incubated with either hybridoma supernatants or ascites, washed at 4° C. extensively, and then stained with FITC anti-mouse IgG. The fluorescent antibody-coated

TABLE 1

| Species | SUPPRESSOR/CYTOTOXIC T CELL DETERMINANTS | | | | | HELPER/INDUCER T CELL DETERMINANTS | | | |
|---|---|---|---|---|---|---|---|---|---|
| | T8 | T5 | T8A | T8B | T8C | T4 | T4A | T4B | T4C |
| Man | 25 ± 4[a] | 20 ± 1 | 25 ± 4 | 25 ± 4 | 25 ± 4 | 41 ± 2 | 41 ± 2 | 41 ± 2 | 41 ± 2 |
| Chimpanzee | 51 | 39 ± 1 | 46 ± 6 | 54 ± 4 | 56 ± 5 | 27 | 35 | 32 | 31 ± 4 |
| Gibbon | 54 ± 11 | 40 ± 5 | 55 ± 10 | 51 ± 8 | 51 ± 10 | 25 ± 1 | 21 ± 4 | 19 ± 4 | <2 |
| Formosan rock macaque | 23 ± 8 | 20 ± 4 | <5 | 27 ± 8 | 28 ± 7 | 28 ± 10 | 27 ± 10 | <2 | 11 ± 6 |
| Owl Monkey | <5 | 26 ± 3 | <5 | <5 | 7 ± 2 | <2 | 45 ± 0 | 43 ± 1 | <2 |
| Common Marmoset | <5 | <5 | 21 ± 2 | <5 | <5 | <2 | 42 ± 4 | <2 | 7 |
| Galago | <5 | <5 | <5 | <5 | <5 | <2 | <2 | <2 | <2 |
| Lemur | N.T. | N.T. | N.T. | N.T. | N.T. | <2 | <2 | <2 | <2 |

*The data are expressed as the percent PBM staining positive ± S.D.

Non-human primate T cells can be used for immunization as follows. First, the cells are isolated from heparinized blood utilizing Ficoli-Hypague and density gradient centrifugation. The marmoset cells are then treated with 0.15M NH$_4$Cl to lyse erythrocytes, washed, resuspended in phosphate buffered saline, and used for immunization and frozen for subsequent screening.

Balb/C or CAF1 mice are then immunized with these cells using standard procedures. The splenocytes obtained are fused in PEG with P3/NS1/1-AG4-1 myeloma cells. Hybridoma culture supernatants reactive with immunizing cells, but unreactive with human B cells or B cell lines, are then selected, and these lines are cloned and recloned by limiting dilution in the presence of feeder cells using standard techniques.

The initial screen is meant to identify antibodies reactive with primate T-cells and unreactive with human B lymphocytes. Subsequent screening then involves the characterization of such antibodies on large panels of human T lymphocytes, including freshly isolated T4 cells are then analyzed on a FACs I, an EPICS V, or a similar instrument, which allow for a precise quantitative assessment of the number of reactive cells.

Anti-2H4

A particular anti-primate cell monoclonal antibody, designated anti-2H4, was produced using standard techniques, as follows.

BALB/c J mice (Jackson Laboratories, Bar Harbor, ME) were immunized with T lymphocyte lines from the cotton top tamarin *Saquinus oedipus*, an herbivorous New World primate species. Peripheral blood lymphocytes from this species were stimulated in vitro with PHA and then maintained in continuous culture with T cell growth factors. Hybridoma cultures containing antibodies reactive with human (E+) cells were selected, cloned, and recloned by limiting dilution methods in the presence of feeder cells; E+ cells are known to be capable of separating T cell derived antibodies from non-T cell derived antibodies. Malignant ascites were then developed and utilized for analysis. The monoclonal antibody anti-2H4 was shown to be of the IgG1 isotype by specificity of staining with fluorescein-labeled goat anti-mouse IgG (Meloy Laboratories, Springfield, VA), and by its failure to be stained by fluorescein-labeled antibodies directed against other subclasses of mouse immunoglobulin.

Preparation of T4+ and T8+ Cell Sets

Human E+ lymphocytes were treated with anti-T4 or anti-T8 monoclonal antibodies and rabbit complement (C) (Pel-Freeze Biologicals). $2 \times 10^7$ cell aliquots were incubated with 1 ml of antibody at a 1:250 dilution for 1 hour at room temperature and then 0.3 ml rabbit C was added to the mixture. The mixture was incubated for another hour in a 37° C. shaking water bath, washed, and residual cells cultured overnight at 37° C. After lysis of cells with anti-T4 and C, >90% of the residual cells were T8+ cells and <5% were T4+ cells. After lysis with anti-T8 and C, >90% of the remaining cells were T4+ cells and <5% were T8+ cells. These two populations will be referred to herein as the T8+ and T4+ sets, respectively.

Analysis and separation of lymphocyte populations with a fluorescence-activated cell sorter To separate T4+ T cells into 2H4+ and 2H4− subpopulations, $80 \times 10^6$ T4+ cells had been cultured overnight were labeled with 4 ml of 1/250 dilution of anti-2H4 and developed with fluorescein-conjugated F(ab')$_2$ goat anti-mouse F(ab')$_2$.

Cytofluorographic analysis of cell populations was performed by means of indirect immunofluorescence with fluorescein-conjugated F(ab')$_2$ goat anti-mouse (Fab')$_2$ on an Epics V cell sorter (Coulter Electronics). Background fluorescence reactivity was determined with control ascites obtained from mice immunized with nonsecreting hybridoma clones. For analysis, all monoclonal antibodies were utilized in antibody excess at dilutions of 1/250 to 1/1000.

This procedure produced two subsets of T4+ cells, a subset exhibiting high reactivity with anti-2H4 (designated "2H4+"), and a subset exhibiting low reactivity with anti-2H4 ("2H4−").

Post-sort viability was greater than 95% by trypan blue exclusion in all instances. Purity of separated T cell subsets was in excess of 95%.

Characterization of Anti 2H4

Figure 2:
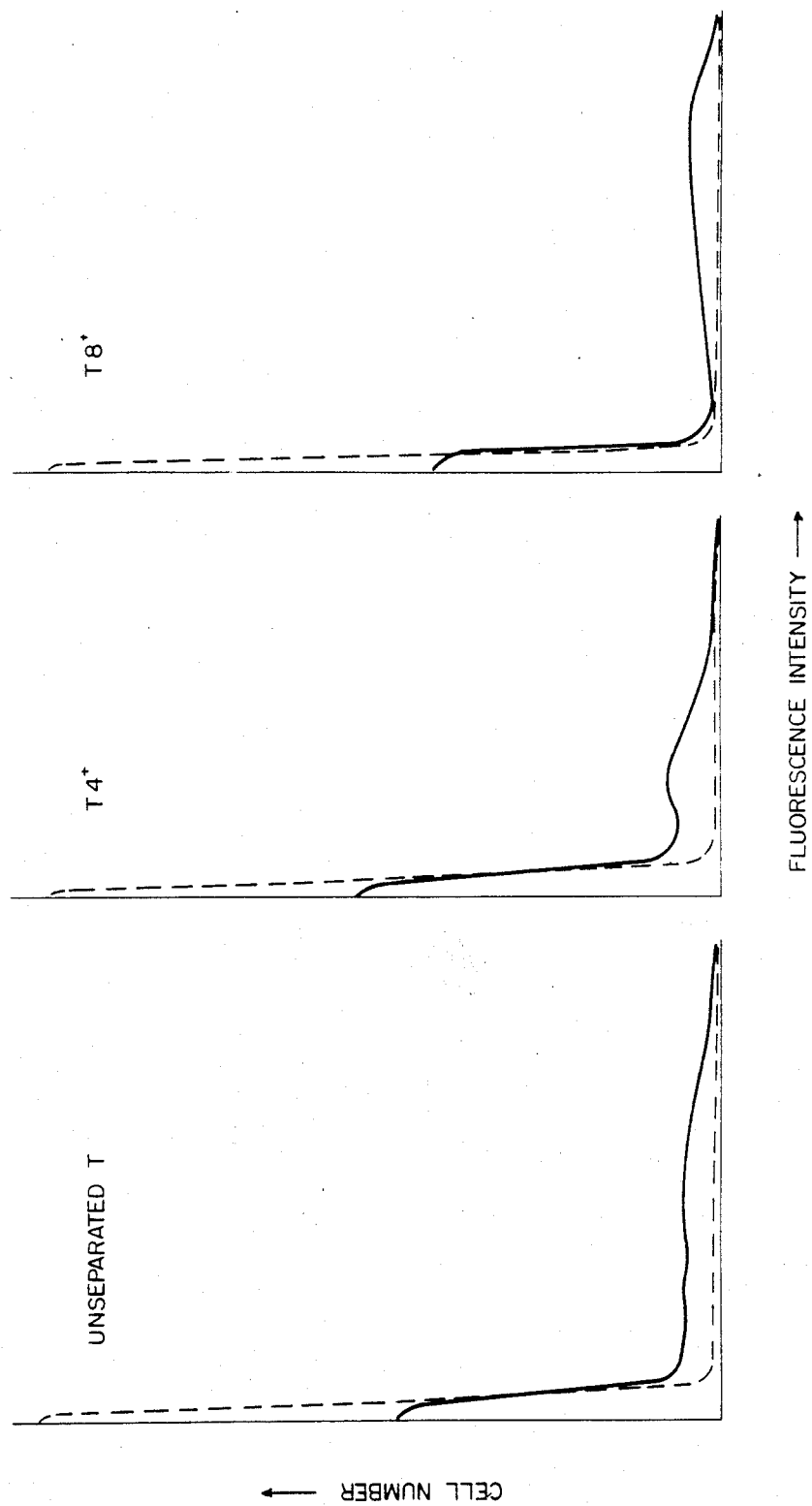
FIG. 2 is a set of graphs showing reactivities of an antibody of the invention with human T cells.

FIG. 2 is a cytofluorographic analysis of unfractionated T, T4+, and T8+ cells with anti-2H4 monoclonal antibody, disployed in logarithmic scale. As shown in FIG. 2, anti-2H4 was found to be reactive with 42±4% (mean±SE, N=20) of peripheral blood human T lymphocytes and reactive with 41±5% (mean±SE, n=15) of T4+ T lymphocytes and 54±4% (mean ±SE, n=15) of T8+ T lymphocytes. Thus, 2H4+ T cells were found in both T4+ and T8+ subpopulations.

The reactivity of anti-2H4 antibody with other human lymphoid cells and cell lines is shown in Table 2, below. Anti-2H4 was found to be reactive with over 30% of both peripheral blood B cells and null cells, only slightly reactive with macrophages obtained by adherence techniques, and unreactive with thymic lymphocytes. Anti-2H4 was also unreactive with 3 of 4 human T cell lines tested, and weakly reactive with JM cell lines, the most mature of four T cell lines which were tested. The data in Table 2 also indicate that reactivity with anti-2H4 was not restricted to cells of the T lineage: four lymphoblastoid B cell lines and two Burkitt's lymphoma lines showed reativity with anti-2H4. In addition, of three hematopoietic cell lines tested, two lines, U-937 and KG-1, were anti-2H4 reactive. These results suggest that the reactivity of anti-2H4 is not restricted to culture cell lines of the T lineage; rather, non-T cells are also anti-2H4 reactive.

TABLE 2

Reactivity of Anti 2H4 Antibody with Human Lymphoid and Cell Lines[a]

| | |
|---|---|
| I. Lymphoid cells | |
| B cells | + |
| Null cells | + |
| M0 | ± |
| II. Thymocytes | − |
| III. T cell lines | |
| HSB | − |
| CEM | − |
| JM | ± |
| Molt4 | − |
| IV. B cell lines | |
| Laz 461 | + |
| Laz 509 | + |
| Laz 388 | + |
| Laz 156 | + |
| Daudi | + |
| Raji | + |
| V. Hematopoietic lines | |
| U-937 | + |
| K562 | − |
| KG-1 | + |

[a]Reactivity of anti 2H4 antibody was determined by indirect immunofluorescence on cytograph, (−) indicates 5% reactivity above background control: (±) indicate 5 to 30% reactivity: (±) indicate 30% reactivity Proliferative response of unfractionated T4+ T cells and T4+2H4− lymphocytes The following procedure was carried out in order to correlate a functional characteristic, proliferative response under varying conditions, with membership in the 2H4+ or 2H4− subset of T4+ cells.

T cells were cultured in RPMI 1640 media with 10% human AB serum, 200 mM L-glutamine, 25 mM HEPES buffer (Microbiological Associates), 0.5% sodium bicarbonate and 1% penicillin-streptomycin. $10^5$ cells per microculture well were tested for proliferative response to an optimal dose of phytohemagglutinin (PHA) (Burroughs-Wellcome Co., Research Triangle Park, NC) and concanavalin A (Con A) (Calbiochem, San Diego, CA). The alloantigen-driven proliferative response was measured concurrently by stimulating with mitomycin C-treated Laz 156, an Epstein-Barr virus-transformed human B lymphoid line. Proliferation to tetanus toxoid (Massachusetts Department of Public Health Biological Laboratories, Jamaica Plain, MA) and mumps antigen (Microbiological Associates) were tested using 10 μg/ml final concentration and a 1:20 dilution, respectively. Macrophages were added to all lymphocyte populations at a 5% final concentration at the initiation of in vitro cultures. Mitogen-stimulated cultures were pulsed after 4 days with 0.15 uCi of tritiated thymidine ($^3$H-TdR) (1.9 Ci/mM sp. act) (Schwarz-Mann, Orangeburg, NY) per cell well; after a 16 hour incubation, the cells were harvested with a Mash II apparatus (Microbiological Associates) and $^3$H-TdR incorporation was measured on a Packard Scintillation Counter (Packard Instrument Co., Downers Grove, IL). Background $^3$H-TdR incorporation was obtained by substituting medium for mitogen. Soluble and cell surface alloantigen-driven cultures were pulsed after 5 days with $^3$H-TdR for 16 hours, harvested, and counted as above.

As shown in Table 3, below, differences in response to Con A and soluble antigens were seen in T4+2H4+ and T4+2H4− T cell populations. In response to Con A, T4+2H4+ T cells incorporated significantly more $^3$H-TdR than did the T4+2H4− population. In response to soluble antigens such as TT and mumps, T4+2H4− T cells incorporated significantly more $^3$H-TdR than did the T4+2H4+ T cell population. These differences between the proliferative response of T4+2H4+ and T4+2H4− populations were significant (P<0.05). They suggest that the major proliferative activity in response to soluble antigens is found in the T4+2H4− T cell population and the major proliferative activity in response to Con A is found in the T4+2H4+ T cell population.

human gamma heavy chain (anti-FC) (gifted by Dr. V. Raso, Dana-Farber Cancer Institute).

As shown in FIG. 2, neither B cells, unfractionated T4+ T cells, or sorted T4+ subsets secreted IgG when cultured alone. In contrast, when unfractionated T4+ T cells and B cells were mixed together and incubated with PWM, 14400±900 ng of IgG were secreted per milliliter of culture supernatant. Incubation of T4+ T cells with anti-2H4 had no effect on the help these cells provided to B cells.

When equal numbers of T4+2H4+ and T4+2H4− cells were added to separate cultures of autologous B cells, the IgG secretion induced by the T4+2H4− T cell subset was approximately 10 times greater than that obtained with the combination of T4+2H4+ and B cell

TABLE 3

Proliferative Responses of Unfractionated T4+ T Cells and T4+2H4+ and T4+2H4− Subpopulations to Nonspecific Mitogens or Antigenic Stimulation

| Proliferative Responses | T4+ T Cells | T4+ T Cells Treated with anti 2H4 and G/M FITC | T4+2H4+ T Cells | T4+2H4− T Cells |
|---|---|---|---|---|
| Exp 1 | | | | |
| Media | 355 ± 156[a] | 707 ± 310 | 787 ± 237 | 504 ± 281 |
| PHA (0.25 ug/ml) | 36852 ± 3268 | 36493 ± 3501 | 32849 ± 2858 | 19605 ± 1949 |
| Con A (30 ug/ml) | 41346 ± 978 | 28691 ± 1643 | 50553 ± 5162[b] | 10522 ± 1729 |
| Con A (60 ug/ml) | 31954 ± 3543 | 27878 ± 1948 | 35732 ± 4526[b] | 8383 ± 535 |
| Tetanus Toxoid | 38056 ± 1022 | 29508 ± 3649 | 8594 ± 1213 | 30232 ± 2527[b] |
| Mumps | 10545 ± 1639 | 9240 ± 478 | 2271 ± 646 | 19832 ± 2138[b] |
| Laz 156 | 88940 ± 8494 | 79962 ± 7498 | 82749 ± 5490 | 67081 ± 6244 |
| Exp 2 | | | | |
| Media | 636 ± 267 | 665 ± 198 | 528 ± 198 | 333 ± 148 |
| PHA (0.25 ug/ml) | 38408 ± 3466 | 31285 ± 2544 | 60399 ± 5343 | 42345 ± 4552 |
| Con A (30 ug/ml) | 10386 ± 1740 | 8214 ± 986 | 17704 ± 1666[b] | 6338 ± 754 |
| Con A (60 ug/ml) | 31800 ± 2566 | 17566 ± 2954 | 47312 ± 3418[b] | 20808 + 1966 |
| Tetanus Toxoid | 8173 ± 827 | 6159 ± 748 | 5437 ± 423 | 18958 ± 1541[b] |
| Mumps | 67129 ± 5694 | 38913 ± 3962 | 7615 ± 685 | 63889 ± 7152[b] |
| Laz 156 | 78110 ± 9632 | 68946 ± 5736 | 141095 ± 5671 | 100703 ± 4065 |

[a]Values are expressed as the mean ± SEM of triplicate samples
[b]Significant differences (p 0.05) on the basis of 95% confidence limits between T4+2H4+ and T4+2114− T cells PWM-stimulated IgG synthesis by B cells co-cultured with T4+2H4+ and T4+2H4− lymphocytes In order to determine whether T cell help for B cell immunoglobulin production was restricted to the T4+2H4+ or T4+2H4− T cell subset, unfractionated T4+ T cells or T4+2H4+ and T4+2H4− cells were mixed with autologous B lymphocytes, stimulated with PWM in vitro, and total IgG production was measured after 7 days in culture.

Unfractionated and separated populations of lymphocytes were cultured in round-bottomed microtiter culture plates (Falcon) at 37° C. in a humidified atmosphere with 5% $CO_2$ for 7 days in RPMI 1640 supplemented with 20% heat-inactivated fetal calf serum (Microbiological Associates), 0.5% sodium bicarbonate, 200 mM L-glutamine, 25 mM HEPES and 1% penicillin-streptomycin. To determine the effect of various subsets of the T4 cells on secretion of IgG by autologous plasma cells, various numbers of unfractionated T4+ T cells or purified T4+2H4+ and T4+2H4− T cell subsets were added to 5×10$^4$ B cells in a volume of a 1 ml. To this was added 0.1 ml of pokeweed mitogen (PWM) (Gibco Laboratories, Grand Island Biological Co., Grand Island, NY) at a 1:50 dilution. Macrophages were added to all populations at a 5% final concentration at the initiation of in vitro cultures. On day 7, cultures were terminated, supernatants were harvested, and IgG secretion into the supernatant was determined by solid phase radioimmunoassay (RIA) utilizing a monoclonal antibody directed at the Fc portion of the (27500±1800 ng vs. 2400±120 ng). Furthermore, a quantitative comparison of the helper function provided by T4+2H4+ and T4+2H4− T cells for B cell IgG production (Table 4, below) showed that the helper effect of T4+2H4− T cells was strikingly greater than that of T4+2H4+ T cells at any number of T cells and B cells tested. Thus, the majority of helper activity for antibody production in response to PWM by B cells was found within the T4+2H4− subset of cells, and the T4+2H4+ had minimal helper effect in this interaction.

TABLE 4

Quantitative Comparison of Helper Function Provided by T4+2H4+ and T4−2H4− T Cells for B cell 1gC Production

| Lymphoid Population | IgG (ng/ml) | | | |
|---|---|---|---|---|
| | Exp 1 | Exp 2 | Exp 3 | Exp 4 |
| B (5 × 10$^4$)[a] | 360[b] | 160 | 640 | 240 |
| B (5 × 10$^4$) | | | | |
| + T4+2H4+ (5 × 10$^3$) | 880 | 140 | 1600 | 2080 |
| + T4+2H4+ (1 × 10$^4$) | 2000 | 720 | 880 | 2800 |
| + T4+2H4+ (2 × 10$^4$) | 1600 | 150 | 960 | 2880 |
| + T4+2H4+ (4 × 10$^4$) | 2400 | 480 | 1760 | 4160 |
| B (5 × 10$^4$) | | | | |
| + T4+2H4− (5 × 10$^3$) | 14400 | 2000 | 1400 | 16000 |
| + T4+2H4− (1 × 10$^4$) | 20400 | 7800 | 8000 | 24000 |
| + T4+2H4− (2 × 10$^4$) | 32000 | 10800 | 12000 | 20000 |
| + T4+2H4− (4 × 10$^4$) | 24400 | 21600 | 8400 | 24000 |
| T4+2H4+ (5 × 10$^4$) | 200 | 100 | 200 | 150 |

TABLE 4-continued

Quantitative Comparison of Helper Function Provided by
T4+2H4+ and T4−2H4− T Cells for B cell IgC Production

| Lymphoid Population | IgG (ng/ml) | | | |
|---|---|---|---|---|
| | Exp 1 | Exp 2 | Exp 3 | Exp 4 |
| T4+2H4− (5 × 10⁴) | 200 | 100 | 200 | 150 |

[a]Figures in parentheses represent the number of lymphocytes of each population added to the culture.
[b]Values are expressed as mean ng/ml of triplicate samples. SEM was always less than 10%.

Effect of T4+2H4+ or T4+2H4− cells on the generation of suppressor effector cells The following procedure was carried out to determine whether these T4+2H4+ and T4+2H4− subsets of cells had any effect on the generation of suppressor function.

Varying numbers of T4+2H4+ or T4+2H4− cells were added to a constant number of B cells (5×10⁴), T4+2H4− or T4+2H4+ T cells (2×10⁴), and T8 cells (1×10⁴) in the presence of PWM. As shown in Tables 5 and 6, below, when increasing numbers of T4+2H4+ cells were added to a constant number of B cells, T4+2H4− cells, and T8 cells, increasing suppression of IgG production was observed (4800 ng vs 300 ng, 32000 ng vs 5000 ng, 24000 ng vs 4800 ng). In contrast, the addition of increasing numbers of T4+2H4+ T cells resulted in enhanced IgG production. These results suggest that T4+2H4+ T cells activate or induce T8+ T cells to become suppressor effector cells.

TABLE 5

Effect of T4+2H4+ or T4+2H4− Subsets on the Generation of Suppressor Effector Cells

| Cell Combinations[a] | T8 cells added | IgG (mg/ml) | | |
|---|---|---|---|---|
| | | Exp 1 | Exp 2 | Exp 3 |
| A. B (5 × 10⁴) + T4+2H4+ (2 × 10⁴) | 0 | 3000[b] | 720 | 4200 |
| | 5 × 10³ | 2300(23)[c] | 288(60) | 4000(5) |
| | 1 × 10⁴ | 560(81) | 888(0) | 2480(41) |
| | 2 × 10⁴ | 280(91) | 200(72) | 500(88) |
| | 4 × 10⁴ | 5(100) | 280(61) | 140(97) |
| B. B (5 × 10⁴) + T4+2H4−(2 × 10⁴) | 0 | 15400 | 1800 | 26000 |
| | 5 × 10³ | 33200(0) | 2800(0) | 40000(0) |
| | 1 × 10⁴ | 21600(0) | 3000(0) | 36000(0) |
| | 2 × 10⁴ | 15600(0) | 2160(0) | 13600(40) |
| | 4 × 10⁴ | 8000(47) | 1240(31) | 5600(78) |

[a]Varying numbers of T8+T cells were added to a constant number of B cells (5 × 10⁴), and to this were added fractionated T4+2H4+ or T4+2H4−T cells (2 × 10⁴) in the presence of PWM. Total IgG production was measured after 7 days.
[b]Values are expressed as mean mg/ml of triplicate samples. SEM was always less than 10%.
[c]Number in parentheses equals % suppression calculated as the following formula:
$$\frac{\text{Control IgG} - \text{IgG observed by the addition of T8 cells}}{\text{Control IgG production}} \times 100$$

TABLE 6

T4+2H4+ T Cells Induce or Activate T8+ T Cells for Effective Suppressor Function

| Cell Combination[a] | Addition of T42H4+ or T42H4− | IgG (ng/ml) | | |
|---|---|---|---|---|
| | | Exp 1 | Exp 2 | Exp 3 |
| | T4+2H4+ added | | | |
| A. B + T4+2H4− + T8 | 0 | 4800[b] | 32000 | 24000 |
| | 5 × 10³ | 2000(58) | 26000(19) | 18000(25) |
| | 1 × 10⁴ | 4000(17) | 14000(56) | 16400(32) |
| | 2 × 10⁴ | 1800(63) | 11000(66) | 4800(80) |
| | 4 × 10⁴ | 300(94) | 5000(84) | N.D. |
| | T4+2H4− added | | | |
| B. B + T4+2H4+ + T8 | 0 | 200 | 540 | 420 |
| | 5 × 10³ | 800(0) | 4000(0) | 2400(0) |
| | 1 × 10⁶ | 1600(0) | 5200(0) | 4600(0) |
| | 2 × 10⁴ | 2000(0) | 9600(0) | 6000(0) |
| | 4 × 10⁴ | 3200(0) | 14000(0) | N.D. |

[a]Varying numbers of T4+2H4+ or T4+2H4− T cells were added to a constant number of B cells (5 × 10⁴) and T4+2H4+ (2 × 10⁴) or T4+2H4− (2 × 10⁴) in the presence of PWM.
[b]Values are expressed as mean ng/ml of triplicate samples. SEM was always less than 10%.
[c]Number in parenthesis equals % suppressor calculated as the following formula:
$$\frac{\text{Control IgG} - \text{IgG observed by the addition of T4 2H4+ or T4 2H4− cells}}{\text{Control IgG production}} \times 100$$

To rule out the possibility that T4+2H4+ T cells are themselves suppressor effector cells, varying numbers of T4+2H4+ or T4+2H4− cells were added to a constant number of B cells (5×10⁴) and T4+2H4+ or T4+2H4− cells (2×10⁴) in the presence or absence of T8+ cells (1×10⁴) with PWM. As shown in Table 7, below, when increasing numbers of T4+2H4+ T cells were added to the mixture of B cells and T4+2H4− cells including T8 cells, marked suppression was seen, as previously shown in Table 6. In contrast, the addition of increasing numbers of T4+2T4− cells to the mixture of B cells and T4+2H4+ cells, with or without T8 cells, resulted in enhanced IgG production. Thus T4+2H4+ cells were not themselves effectors of suppression; rather they induced or activated T8+ cells to suppress the immune response.

TABLE 7

T4+2H4+ T Cells are not Themselves Suppressor Effector Populations

| Cell Combination[a] | Addition of T4+2H4+ or T4+2H4− | IgG (ng/ml) Exp. 1 | IgG (ng/ml) Exp. 2 |
|---|---|---|---|
| | T4+2H4+ added | | |
| A. B+T4+2H4− | 0 | 3280[b] | 2100 |
| | $5 \times 10^3$ | 3240(1) | 3060(0) |
| | $1 \times 10^4$ | 3240(1) | 1995(5) |
| | $2 \times 10^4$ | 2400(26) | 2090(1) |
| B. B+T4+2H4− + T8 | 0 | 4400 | 2040 |
| | $5 \times 10^3$ | 3600(18) | 1400(31) |
| | $1 \times 10^4$ | 2800(36) | 840(59) |
| | $2 \times 10^4$ | 920(79) | 440(78) |
| | T4+2H4− added | | |
| C. B+T4+2H4+ | 0 | 720 | 320 |
| | $5 \times 10^3$ | 1040(0) | 510(0) |
| | $1 \times 10^4$ | 1080(0) | 1510(0) |
| | $2 \times 10^4$ | 1820(0) | 1940(0) |
| D. B+T4+2H4+ + T8 | 0 | 280 | |
| | $5 \times 10^3$ | 720 | |
| | $1 \times 10^4$ | 880(0) | N.D. |
| | $2 \times 10^4$ | 1320(0) | |

[a] Varying numbers of T4+2H4+ or T4+2H4− T cells were added to a constant number of B cells ($5 \times 10^4$) and T4+2H4+ ($2 \times 10^4$) or I4+2H4− ($2 \times 10^4$) in the presence of PWM with or without T8 cells ($1 \times 10^4$).
[b] Values are expressed a mean ng/ml or triplicate samples. SEM was always less than 10%.
[c] Number in parentheses equals % suppression as described in Table 5.

Correlation with disease

Flow cytometry tests were carried out on lymphocytes taken from two human patients suffering from SLE. One of the patients exhibited a substantial decrease in the size of T4+2H4+ subset, compared to normal subjects, while the second SLE patient exhibited a complete absence of the T4+2H4+ subset. These results suggest the possibility that the loss of these inducers of suppression is a causal factor in this autoimmune disease.

Deposit

Hybridoma cells producing anti-2H4 antibody have been deposited in the American Type Culture Collection, Rockville, Md., and given ATCC Accession No. HB8570.

What is claimed is:

1. A method of distinguishing subsets within a plurality of human cells comprising
   producing a monoclonal antibody to a non-human primate cell,
   contacting said monoclonal antibody with said human cells, and
   distinguishing said subsets on the basis of different degrees of reactivity with said monoclonal antibody.

2. The method of claim 1 wherein said non-human primate cells are T cells.

3. The method of claim 1, further comprising the steps of
   immunizing a plurality of animals with the cells of a first said subset to produce a plurality of different hybridomas producing different monoclonal antibodies,
   testing the reactivity of said antibodies with cells of a second said subset not used in said immunization, and
   selecting a said antibody which has less reactivity with said second subset than with said first subset.

4. The method of claim 1 wherein said human cells are T cells.

5. The method of claim 4 wherein said T-cells are T4+ cells or T8+ cells.

6. The monoclonal antibody produced by the hybridoma cell given ATCC Accession No. HB8570.

7. The hybridoma cell having the identifying characteristics of ATCC Accession No. HB8570.

* * * * *